(12) United States Patent
Gray (10) Patent No.: US 9,980,819 B2
(45) Date of Patent: May 29, 2018

(54) VASCULARIZED POROUS METAL ORTHOPAEDIC IMPLANT DEVICES

(71) Applicant: Robert R. Gray, Glencoe, IL (US)

(72) Inventor: Robert R. Gray, Glencoe, IL (US)

(*) Notice: Subject to any disclaimer, the term of this patent is extended or adjusted under 35 U.S.C. 154(b) by 0 days. days.

(21) Appl. No.: 15/234,112

(22) Filed: Aug. 11, 2016

(65) Prior Publication Data

US 2017/0027699 A1    Feb. 2, 2017

Related U.S. Application Data

(62) Division of application No. 13/793,395, filed on Mar. 11, 2013, now Pat. No. 9,427,319.

(Continued)

(51) Int. Cl.

| A61L 27/56 | (2006.01) |
|---|---|
| A61F 2/06 | (2013.01) |
| A61L 27/04 | (2006.01) |
| A61L 27/06 | (2006.01) |
| A61F 2/28 | (2006.01) |

(Continued)

(52) U.S. Cl.
CPC .......... *A61F 2/30771* (2013.01); *A61B 17/68* (2013.01); *A61B 17/8061* (2013.01); *A61F 2/06* (2013.01); *A61F 2/28* (2013.01); *A61F 2/2846* (2013.01); *A61F 2/32* (2013.01); *A61F 2/3836* (2013.01); *A61F 2/4202* (2013.01); *A61F 2/4261* (2013.01); *A61L 27/047* (2013.01); *A61L 27/06* (2013.01); *A61L 27/56* (2013.01); *A61M 27/002* (2013.01); *A61F 2002/2825* (2013.01); *A61F 2002/2853* (2013.01); *A61F 2002/3092* (2013.01); *A61F 2002/3093* (2013.01); *A61F 2002/30677* (2013.01); *A61F 2002/30784* (2013.01); *A61F 2002/30952* (2013.01); *A61F 2002/30962* (2013.01); *A61F 2002/30981* (2013.01); *A61F 2002/30985* (2013.01); *A61F 2002/4271* (2013.01); *A61F 2310/00023* (2013.01); *A61F 2310/00131* (2013.01); *A61F 2310/00161* (2013.01); *A61F 2310/00407* (2013.01)

(58) Field of Classification Search
CPC .... A61F 2/06; A61F 2/064; A61F 2/28; A61F 2/2846; A61F 2/4261; A61F 2002/2817; A61F 2002/2853; A61F 2002/2846; A61F 2002/30494; A61F 2002/30535; A61F 2002/30667; A61F 2002/30691; A61F 2002/30766; A61F 2002/30771; A61F 2002/30772; A61M 27/002

See application file for complete search history.

(56) References Cited

U.S. PATENT DOCUMENTS

| 4,880,006 A | 11/1989 | Albrektsson et al. |
|---|---|---|
| 5,527,856 A | 6/1996 | Rhee et al. |

(Continued)

*Primary Examiner* — Thomas J Sweet
*Assistant Examiner* — Christie Bahena
(74) *Attorney, Agent, or Firm* — Fitch, Even, Tabin & Flannery, LLP (57) ABSTRACT

An osteoconductive vascularized porous metal implant device and method for implanting the vascularized device are described herein. The vascularized implant device comprises an implant which is porous titanium, tantalum or other metal which is biocompatible with the mammalian body and at least one vascular conduit which connects the porous implant to an animal vasculature, such as a human vascular system.

12 Claims, 5 Drawing Sheets

Related U.S. Application Data (60) Provisional application No. 61/749,656, filed on Jan. 7, 2013, provisional application No. 61/693,355, filed on Aug. 27, 2012.

(51) Int. Cl.

| | | |
|---|---|---|
| *A61F 2/30* | (2006.01) | |
| *A61F 2/42* | (2006.01) | |
| *A61M 27/00* | (2006.01) | |
| *A61B 17/68* | (2006.01) | |
| *A61B 17/80* | (2006.01) | |
| *A61F 2/32* | (2006.01) | |
| *A61F 2/38* | (2006.01) | |

(56) References Cited

U.S. PATENT DOCUMENTS

| | | | |
|---|---|---|---|
| 6,409,764 | B1 | 6/2002 | White et al. |
| 6,425,923 | B1 | 7/2002 | Stalcup et al. |
| 6,440,166 | B1 | 8/2002 | Kolluri |
| 6,979,336 | B2 | 12/2005 | Dumiak |
| 7,998,735 | B2 * | 8/2011 | Morrison ................ A61F 2/062 |
| | | | 435/325 |
| 8,053,220 | B2 | 11/2011 | Harlow et al. |
| 8,197,551 | B2 | 6/2012 | Swain et al. |
| 8,778,029 | B2 | 7/2014 | Baumgart |
| 2005/0119745 | A1 | 6/2005 | Tabata et al. |
| 2007/0179609 | A1 | 8/2007 | Goble et al. |
| 2008/0300684 | A1 | 12/2008 | Shelokov |
| 2009/0005868 | A1 | 1/2009 | Gundlapalli et al. |
| 2009/0018657 | A1 | 1/2009 | Linares |
| 2009/0192610 | A1 | 7/2009 | Case et al. |
| 2009/0326515 | A1 | 12/2009 | Kagan |
| 2010/0042214 | A1 | 2/2010 | Nebosky et al. |
| 2010/0168689 | A1 * | 7/2010 | Swain ................ A61M 1/0088 |
| | | | 604/313 |
| 2010/0168867 | A1 * | 7/2010 | Swain ................ A61F 2/28 |
| | | | 623/23.49 |
| 2011/0137418 | A1 | 6/2011 | O'Neil et al. |

* cited by examiner

VASCULARIZED POROUS METAL ORTHOPAEDIC IMPLANT DEVICES

CROSS-REFERENCE TO RELATED APPLICATIONS

This application is a divisional of prior application Ser. No. 13/793,395, filed Mar. 11, 2013, which claims priority to Application No. 61/749,656 filed Jan. 7, 2013, and Application No. 61/693,355, filed Aug. 27, 2012, which are hereby incorporated herein by reference in their entirety.

FIELD

The present application relates to medical devices and methods, and more particularly, to vascularized porous metal orthopaedic implants.

BACKGROUND

In orthopaedic surgery, bones are often fused together to prevent pain, improve function, and heal injuries. In settings of impaired blood supply, massive bone loss, or complicated trauma, techniques such as bone grafting or implanting metal are used to facilitate fusion or reconstruction. However, bone grafts have limitations of strength and available amounts of donor bone. Metal implants are also imperfect because if they are not securely fixed in living bone, they go onto fatigue and failure. In addition, both bone grafting or implanting can be problematic when there is inadequate blood supply to the repaired region including the bone or implant. Insufficient blood supply increases the risk of infection and limits the amount of bone formation in and at the interface of the implant with the bone (osteogenesis).

Some have tried vascularized bone grafting where blood is supplied by veins or conduits naturally forming part of the bone graft. This technique uses natural/actual bone with an attached blood vessel where the bone is harvested from the patient or donor, and then the harvested bone is used to fuse or reconstruct bones. It is known that the increased blood supply speeds healing, reduces infection, and increases strength. Unfortunately, however, current vascularized bone grafts must be harvested from the patient, increasing morbidity, lengthening recovery time, and increasing surgical complexity, such as infection risk. In addition, the number, size and shape of current vascularized bone grafts are limited. Lastly, these grafts are not usually taken from another animal or person due to immunologic graft-rejection issues.

As can be seen, there is a need for a system that combines the strength of a metal implant with a more effective blood supply than the supply provided by native vascularized bone implant or graft. It may be desirable to minimize large avascular regions in a bone graft or implant which can harbor bacteria. It also may be desirable to avoid the risk and disadvantages which currently exist with a massive bone harvest with later use of the bone harvest as a bone graft or implant. Even further, even if a bone harvest could be readily used without regard to problems associated with the act of harvesting bone, there is a need and advantages to providing an implant that can be made in a plurality of shapes and sizes that would not be available or at least readily obtained from a harvest of natural bone from a patient.

The advantages of a vascularized porous metal implant device include (1) the device not being limited by size or shape as compared to naturally harvested bone, (2) there is not a breakdown of the metal implant, (3) the device promotes bone growth into the core of the implant across a fusion gap between two pieces of bone being fused or connected and (4) the device lowers infection rate of implant by increasing blood circulation throughout the implant. These and other advantages will become apparent from the discussion set forth below.

SUMMARY

In one form, an osteoconductive vascularized porous metal implant device and method for implanting the vascularized device are described herein. The vascularized porous metal implant device comprises an implant which is porous titanium, tantalum or other metal which is biocompatible with the mammalian body and at least one vascular conduit which connects the porous metal implant to a mammalian vasculature, such as a human vascular system. The osteoconductive vascularized porous metal implant device is implanted into a host in need thereof, connected to the vascular system, and is used for reconstruction of bone defects or joint defects by removing diseased or injured bone(s) and attaching the implant which then promotes bone healing by bone fusion growth into the porous metal implant by virtue of exposing bone to blood being conveyed into the metal implant while also reducing fatigue and implant failure.

According to one form, the metal implant has a porosity that provides internal voids which form at least about 50 volume percent of the implant and preferably from about 70 to about 80 volume percent of the implant. At least one vascular conduit effects blood flow into the porous metal implant by having the vascular conduit extend into and below the outer surface of the metal implant to effect blood flow from the vascular system of the host who receives the implant device into the internal portions of the porous metal implant. This provides blood flow internal to the porous metal implant, and as a result, effects exposure of blood to bone interfacing with the implant and effects bone growth into the pores of the implant for improved strength and durability of the bone graft created by the implant connecting or interfacing two sections of bone. According to one form, it is hypothesized that blood flows through the porous implant at least as a result of capillary action.

In one form, after grafting the vascularized porous metal implant device into the reconstracted area, the enhanced blood flow into the interface between the bone and implant increases bone growth internal to the porous metal implant and improves the strength of the graft after insertion thereof by at least about 4×, and even more than 16× as compared to implanting the same porous metal implant which has not been vascularized for increased blood flow internal to the porous implant. According to one form, this increased blood flow is at least 10× and even more than 100× the blood flow internal to the porous implant as compared to known porous metal implants that have not been connected to the vascular system as described herein.

According to one form, the porous titanium or porous tantalum can be foam implants, for example, comprising pores of about 300 nm to about 1300 nm depth and breadth of each pore, preferably about 400 nm to about 800 nm, more preferably about 700 nm, which are commercially available from Zimmer, Inc., Warsaw, Ind., USA. In another important aspect, the vascular conduit is made from polytetrafloro ethylene (PTFE) which has been extruded and which is commercially available from Atrium Medical, Hudson, N.H., USA. Other polymeric materials may also be suitable for the vascular conduit including polyethylene terephthalate and other woven polyesters. The diameter of these conduits is in the range of from about 3 mm to about 9 mm.

In one form, the number of vascular conduits, positioning the conduits and the number, size and volume of the pores are effective to provide a blood flow that is at least 10× and can supply even more than 100× blood flow internal to the porous implant as compared to the same porous metal implants that have not been connected to the vascular system as described herein. According to one form, the number of vascular conduits, positioning of the conduits, and the number, size and volume of the pores are effective to provide an enhanced blood flow into the internal voids of the metal implant and the interface between the bone and implant. After grafting the vascularized porous metal implant device into the reconstructed area bone growth internal to metal implant, blood flow is increased and improves the strength of the graft after insertion by at least about 4×, and even more than 16× after about 4-6 weeks as compared to implanting the same metal implant which has not been vascularized for increased blood flow internal to the porous implant.

In accordance with one form, the increased blood flow into the implant is important in respect to large implants. The risk of catastrophic implant failure increases with the size of the implant because bone has difficulty in achieving durable and/or strong connection between a large implant and existing bone because the ratio of the surface area of the bone/implant interface to the overall size of the implant is low. Porous implants increase the surface area, but bone ingrowth is still limited to the periphery of the implant. However in a small implant, the ratio of the surface area of the bone/implant interface to the overall size of the implant is larger. There is more peripheral surface area to allow for ingrowth and increase stability. In fact, if the small implant is porous, bone ingrowth from the edges may meet in the center, effectively completely incorporating the implant. However, even in porous implants, the depth of bone ingrowth is not more than several millimeters and implants with a radius of greater than approximately 3 mm will not achieve ingrowth into the center of the implant.

The lack of such ingrowth, particularly in large implants, increases the risk of implant failure taught in the prior art. In one form, using the vascularized, porous implant device described herein overcomes the limitation of size and shape of implants because of relatively high mechanical loading or high torque applications, and/or large implants. Hence in an important aspect, when the ratio of the surface area between the bone and implant interface to the overall size of the implant is less than about 0.75 use of the vascularized implant device is particularly useful in providing the increased strength and blood flow described herein.

Also described herein is a method of performing orthopedic surgery which includes implanting the porous metal implant and connecting at least one vascular conduit to the vascular system of the host.

BRIEF DESCRIPTION OF THE DRAWINGS

FIG. 1b is a side perspective view of the implant device of FIG. 1a;

FIG. 3a is a perspective view of an implant device inserted in a wrist of a patient;

FIG. 3b is an enlarged view of the implant device of FIG. 3a;

FIG. 4b is an enlarged view of the implant device of FIG. 4a;

DETAILED DESCRIPTION

The following detailed description is of currently contemplated modes of carrying out exemplary embodiments of the present application. The description is not to be taken in a limiting sense, but is made merely for the purpose of illustrating the general principles.

In one form, a porous implant device is provided which includes a rigid, unbendable, non-flexible, porous implant, such as a porous metal implant, and at least one biocompatible conduit. The implant is non-flexible, but also exhibits a modulus of flexibility about the same as human bone. The porous metal implant may be made from a variety of different materials that are suitable for implantation and use, such as in mammals. For example, in one form, the porous metal implant includes at least one metal selected from the group consisting of porous titanium, porous tantalum or metal-alloy comprising porous titanium or tantalum implants. Other materials besides metals may also be utilized which can be manufactured with pores and/or channels to permit blood flow and/or bone growth through at least a portion of the implant. In one preferred form, the porous implant has sufficient strength to support bones in a desired implant location. For example, an implant near a hip joint may be desired to have a higher strength than an implant in other locations. Finally the implant is more stable and does not break break down relative to vascularlized bone harvested from the host or allograft bone (from a dead person) over the same comparative time periods.

According to one form, the porous implant, such as made from titanium or tantalum, can be foam implants. For example, the foam implants may comprise pores and/or channels that are about 300 nm to about 1300 nm in depth and breadth of each pore, preferably about 400 nm to about 800 nm, more preferably about 700 nm. Such implants are commercially available, such as from Zimmer, Inc. Such implants may be suitable for achieving bony ingrowth. The rigid, non-flexible material described above, provides structural strength and stability within the implant region of the bone. Additionally, in one form, the pores described above are throughout the entire implant, and not limited to the surface.

There are numerous processes for production of porous metal implants. For example, in one form, a reticulated vitreous carbon network is prepared using a chemical vapor deposition process to layer elemental metal onto the underlying carbon structure. Such processes are used by Zimmer.

Other processes may involve some form of forging, three-dimensional printing (3DP) or other forms of manufacture. Three-dimensional printing can be used to optimize or customize the design of efficient channels. Three-dimensional printing functions by repeated deposition of powdered material in thin layers and printing of a binder material on each powder layer to selectively bind the powder deposited in that layer. This process is repeated layer after layer until the whole three-dimensional part is completed according to sliced data from a CAD model. A CAD model design is converted into alternative computer language files, which is sliced into thin cross-sectional layers and sintered at a range of 1200° to 1500° C. The use of 3DP provides a tool for designing well-defined channels for circulation throughout the implant in a sterile environment.

Alternatively, vascular channels within an implant can be drilled or cut, or incorporated in the initial forging. The sizes of the channels are variable in size, and will be created in a branching, reticular fashion to mimic native nutrient arteries. The branching patterns are based on studies of nutrient arteries in bone specimens as well on known fractal mathematical relationships of vessel arborization. In one form, the range is about 0.5-5 mm in diameter.

The biocompatible conduit, such as in the form of a vascular conduit, may be made from a variety of different materials in a variety of different sizes, lengths, gauges and the like. For example, in one form, the vascular conduit may be a biocompatible polymer conduit such as a PTFE (polytetrafluoroethylene) vascular conduit, such as made under the name GORETEX®, to impart vascularity throughout the implant. The vascular conduit can be attached to the implant by a number of ways, by way of example, gasket, O-ring, stitching, staples, glue, and other attachment means known in the art.

In one form, the polymeric vascular graft functions as a conduit for attaching blood vessels to one another and/or to the implant. This conduit allows connection of the porous metal implant to a local blood vessel to allow vascular ingrowth. In one form, the vascular conduit may provide blood flow into the porous metal implant by having the vascular conduit extend into and below an outer surface of the porous metal implant. Such a combination may provide a greater blood supply and progenitor cells that form bone at least partially though and around the implant, thereby facilitating faster healing, healing of larger defects, and improved immunologic protection through greater contact with the humeral immune system in an animal or human patient. In addition, in one form, such a combination may eliminate morbidity of bone graft harvest and expands the size and shape of grafts available.

Implants can be provided with the polymeric vascular conduit pre-attached, but depending on the configuration, providing implants with multiple access points for graft attachment as well as a clamp and O-ring connection may allow for intraoperative vascular graft placement after the structural metal component has already been implanted. This versatility can allow the flexibility needed in situations of aberrant anatomy or when the initial operative plan encounters difficulties. Such equipment can come in a prepared kit with the implant that includes the instrumentation needed both to place the implant as well as tools to modify it such as heavy-duty bolt cutters or snips for fashioning the implant in situ, polymeric conduits of varying dimensions to accommodate differing host vessel calibers, microsurgical instruments for preparing the anastomosis between the implant and the host vasculature, O-ring, gasket, sleeve-and-stem, and bidirectional couplers used to affix the polymeric conduit to different locations in the implant, chemical and biological additives such as heparin, bone morphogenic protein, procollagen, vascular endothelial growth factor, and the previously named growth factors to aid in preparing the anastomosis and priming the implant for vascular invasion and osseous integration. Many of these instruments may be packaged in the same container for sterile processing, though several of the implantables such as the grafts and the additives such as the chemicals and growth factors may come separately packaged in sterile packaging or "peel-packed" for use as needed during the surgical procedure.

Further, the vascularized implant device may come in the form of a kit. The kit may include one or more porous implants, one or more vascular conduits and at least one instrument for assisting in installation of the vascularized implant device. For example, the kit may include a plurality of differently sized or shaped porous implants. Similarly, the kit may include a plurality of different vascular conduits which may have different lengths, gauges, diameters and the like so the kit may be configured for the specific use.

It should be noted that the porous implant may be manufactured to have a variety of sizes and shapes. For example, such shapes may include, but are not limited to, rings, barbells, square, rectangular, wedge-shaped, irregular shaped, and the like. The actual shape may be prepared in accordance with the desired use. For example, different bone implant locations necessitate different shapes and configurations.

Described also is a method for generating implants of a specific size and shape for various applications. Libraries of bone specimens exist in several locations that have been used for anthropological and medical research. Bones from these libraries can be evaluated using cross-sectional imaging such as computerized tomography for attributes relating to their size and shape as well as the patterns of intraosseous vascular channels. This data may be used along with computer aided design techniques to program 3DP or other fabricating machines to produce implants that mimic these properties. Further, the patient's own anatomy may be used in a similar fashion as their limb or a portion of their spine may be imaged and the data from that used to fashion custom-made implants.

The porous metal implant devices described herein may be used with vascular conduit for arthrodesis, joint fusion, small bone alignment (such as intercarpal fusion, foot and ankle fusion, wrist fusion, knee fusion, etc.) grafting large segments together including an above critical size defect replacement with an arthroplasty (such as oncologic hip and/or knee prosthesis). Also described herein are methods of revascularization and reconstruction of bones with compromised blood supply such as scaphoid or femoral head avascular necrosis; methods of reconstruction with delivery of antibiotics from the blood stream and throughout the recipient site implants for reconstruction of critical defects in the setting of oncologic resection, trauma, and massive infection.

The porous metal implant may be configured to provide the structural rigidity and support to facilitate bone fusion or healing. The vascular channels and/or pores within the metal implant improve blood flow from the center of the implant to the periphery in a fashion similar to living bone.

In one form, coating portions of the vascular channels of the porous implant and/or the vascular conduit with specific growth factors such as VEGF (Vascular Endothelial Growth Factor), antibiotics or other infection inhibiting or healing medicaments, or hydroxyapatite which can encourage blood vessel formation and differentiation of progenitor cells preferentially into osteoblastic cells that form bone.

Further, in one optional form, the implant device may also include one or more further vascular conduits which may be used as an outlet conduit from the implant. In other words, as blood flows from an inlet vascular conduit and through the porous implant, a further conduit may be provide to allow blood to be removed from the porous implant. Such a system can be used in the case of excess blood flow, to allow blood which has already contacted the bone to pass through, and the like. The outlet conduit may be connected to further vasculature and/or simply lead away from the implant device to other locations.

In addition to the benefits of improving fusion mechanics, the combination of features may be especially advantageous in various areas of the body. For example, areas such as the wrist which are relatively subcutaneous may be suitable for the implant device. Many fusion implants, especially those for total wrist fusion, lie external to the bone and create problems with their prominence, often necessitating secondary surgeries for implant removal. The described disclosure minimizes the need for secondary surgeries by fusing throughout the host bone.

Partial wrist arthrodesis with scaphoid excision is a common surgical procedure used to address arthrosis and pain created by various types of ligamentous instability. Once soft-tissue procedures have failed and early arthrosis and pain have developed, this procedure offers a durable, stable wrist that allows for pain-free activity. While this obviously has some limited motion compared with the uninjured wrist, it has much more motion than the definitive option of total wrist fusion. This makes it very appealing to surgeons and patients.

Perhaps the greatest complication with certain surgeries is failed fusion (pseudarthrosis). Most surgeons use a dorsal approach to the wrist and the hardware is all placed dorsally. In addition to the issues of symptomatic hardware, this dorsal placement can also cause the carpal bones to gap open on the volar surface, which can cause pseudarthrosis.

Figure 1A:
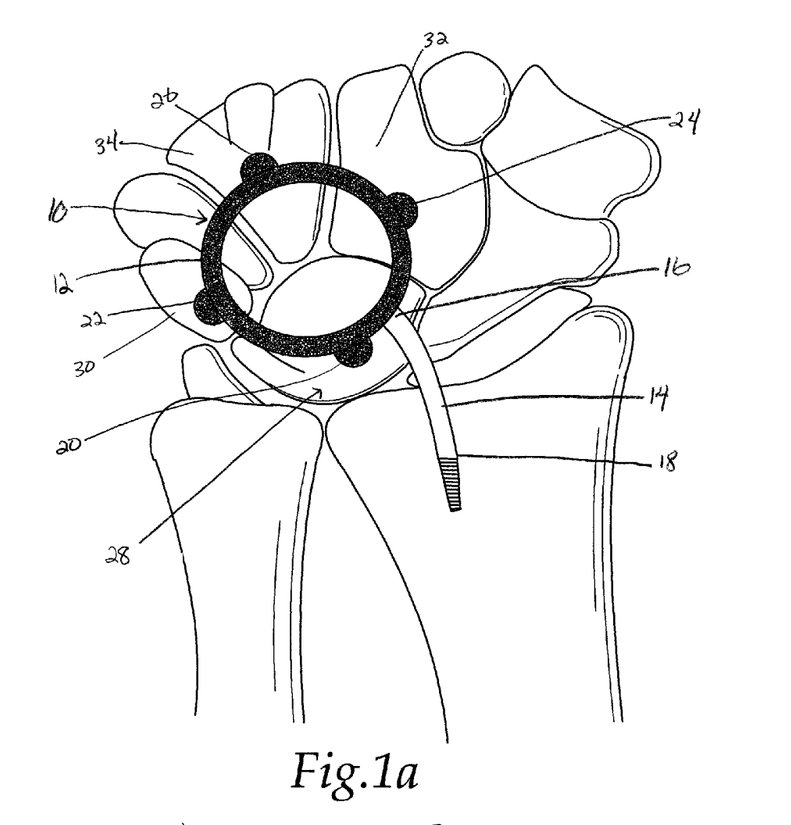
FIG. 1a is a top perspective view of a four corner implant device as affixed to various wrist bones.

Referring to FIG. 1a, one form of an implant device 10 is shown. The implant device 10 is generally a four-corner fusion implant which may be suitable for pseudarthrosis. The implant device 10 includes a porous metal implant 12 and a vascular conduit 14. A first end 16 of the vascular conduit is operably coupled to the implant 12 while a second end 18 is configured to be operably couple to a vascular system (not shown).

Figure 1B:
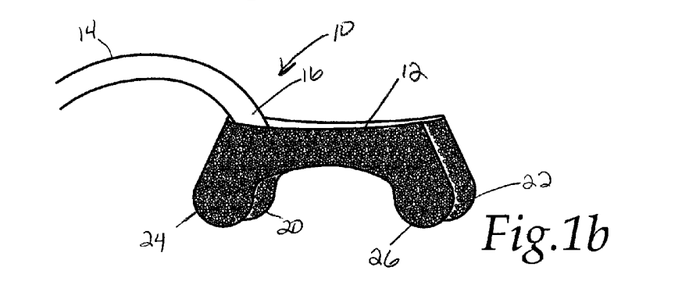

As seen in FIGS. 1a and 1b, the implant 12 includes four posts 20, 22, 24, 26 which may be configured for coupling to various portions of the anatomy, such as the lunate 28, triquetrum 30, capitate 32, and hamate 34 bones. The implant 12 may be inset into the four bones 28, 30, 32, 34, once they are prepared for fusion with high-speed bur (not shown). A guide jig (not shown) may be used to bur a trough for placement of the implant in a press-fit fashion. This press-fit and friction created by deliberately slightly undersizing the radius of the burred trough may be used to provide stability. In addition, because the implant is intraosseous, the moment arm is shortened, and the stability increased.

Figure 2:
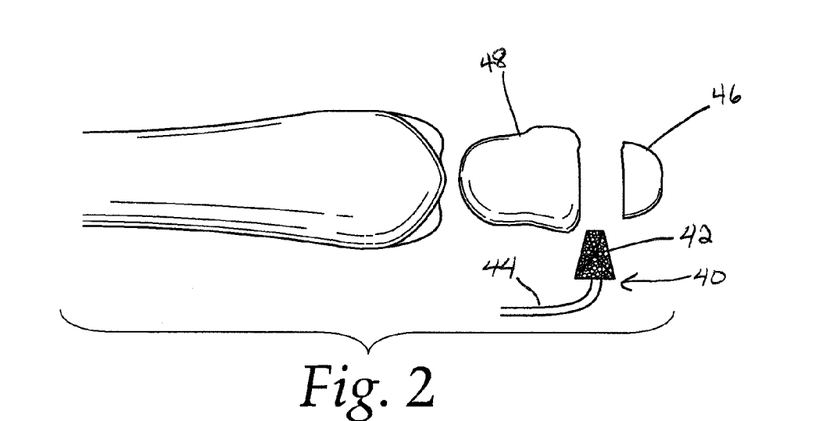
FIG. 2 is a perspective view of another form of an implant device.

Referring to FIG. 2, a further implant device 40 is shown. The device 40 includes an implant 42, such as a porous metal implant, and a vascular conduit 44. As seen in FIG. 2, the implant 42 has a different shape than implant 10 shown in FIG. 1a. Implant 40 has a different shape for coupling different bones such as bone 46 and bone 48. In this regard, the implant 42 is generally wedge shaped to accommodate different anatomical shapes.

For example, implant device 40 may be used to treat avascular necrosis of the proximal pole. The implant device 40 is connected with the radial artery using a microvascular end-to-side anastamosis in the same fashion as is currently employed with vascularized bone autografting. In one form, both the conduit 44 and the implant 42 may be treated with vascular endothelial growth factor (VEGF), Epidermal growth factor (EGF), prostaglandin E2 (PGE2), Insulin-like growth factor (IGF 1 or 2), or Osteoprotegerin (OPG), optionally combined with hydroxylapatite (HA), to aid in the revascularization of the scaphoid. The same implant and method may be employed in the treatment of avascular necrosis of the lunate (Kienbock's disease) and scaphoid (Preiser's disease).

Figures 3A, 3B:
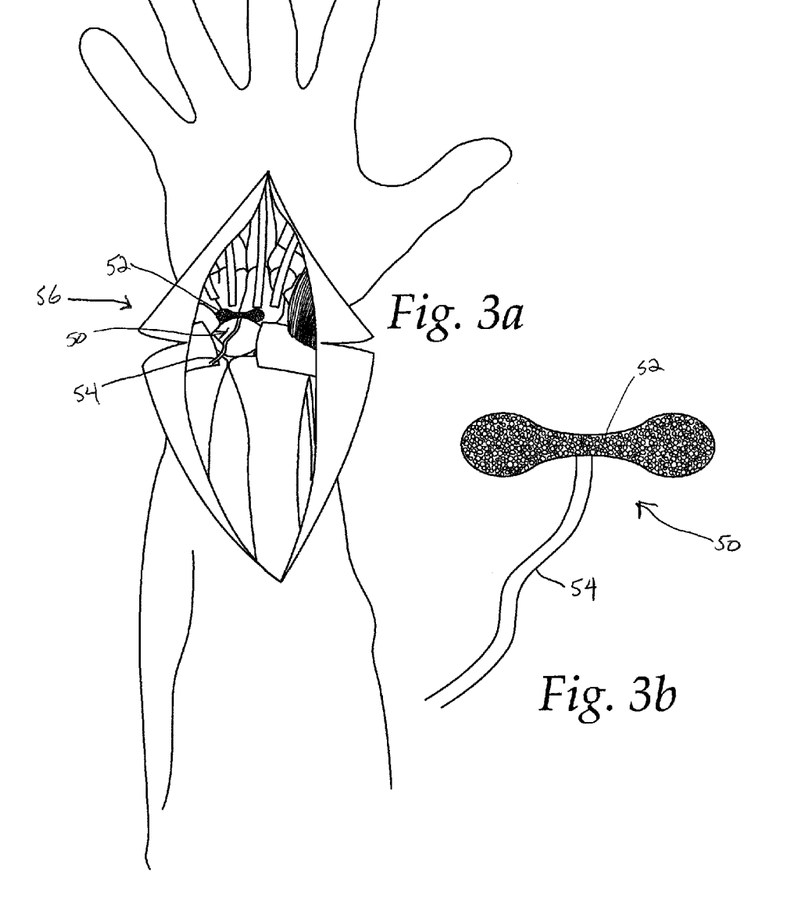

Referring now to FIGS. 3a and 3b, a further form of device is shown as implant device 50. Implant device 50 include implant 52, such as a porous metal implant, and a vascular conduit 54. As seen in FIGS. 3a and 3b, the implant 52 is generally barbell shaped and may be used with various anatomies, such as in a wrist area 56. The implant 52 is barbell shaped to operably couple at least two bones.

With respect to scaphoid nonunion and malunion, the retrograde blood supply of the scaphoid and unique shape predispose it to both avascular necrosis of the proximal pole and collapse into what is termed a "humpback" deformity. Numerous surgical techniques have been described to restore the length and bone stock of the scaphoid as well as to increase vascularity to the proximal pole.

Much in the same way that a vascularized bone autograft is used for scaphoid nonunions with humpback deformity, this technique describes an implant to restore the alignment and blood supply of the scaphoid, wherein a porous titanium foam implant is machined to fit the scaphoid, such as in a dumbell shape shown in FIGS. 3a and 3b, and implanted using a volar surgical approach. This allows reduction of the fracture and eliminates one of the primary difficulties encountered with current fixation methods-joint penetration with the hardware.

Figure 4A:
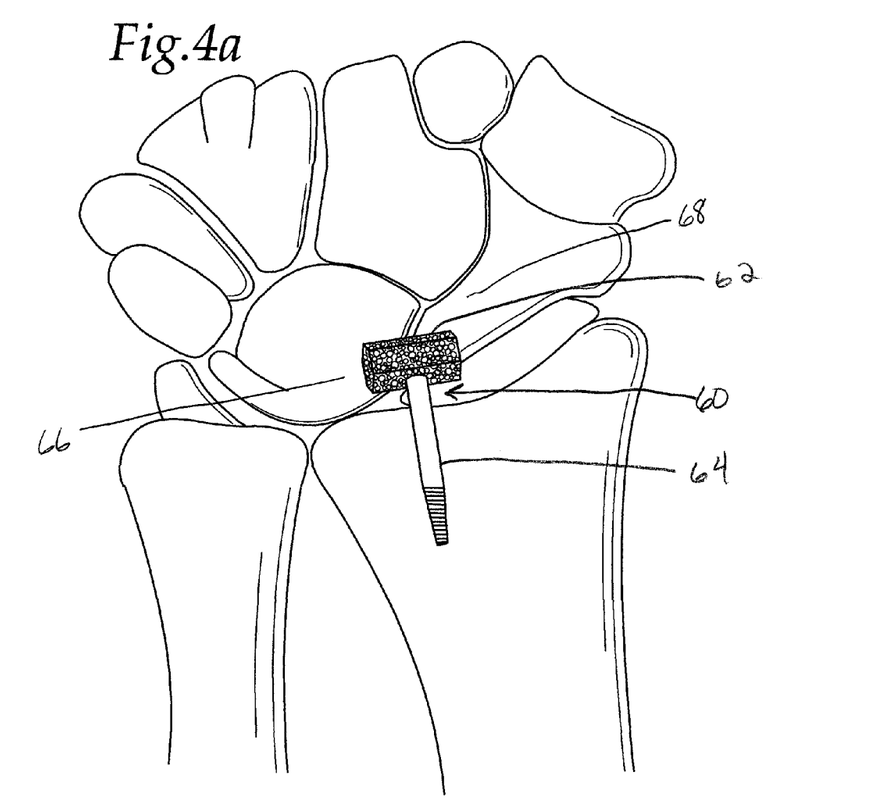
FIG. 4a is a perspective views of a hexagonal cross sectional form of an implant device.
Figure 4B:
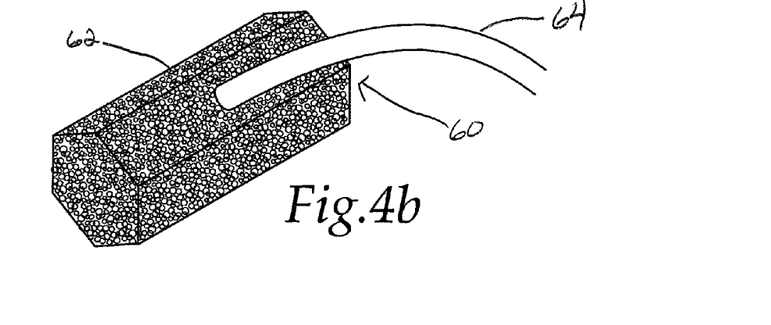

A further form of device is shown in FIGS. 4a and 4b, such as in the form of implant device 60. Implant device 60 include implant 62, such as a porous metal implant, and a vascular conduit 64. As seen in FIGS. 4a and 4b, the implant 62 is generally in the form of a prism with a hexagonal cross-section. In this regard, implant device 60 may be used in a variety of anatomies, such as a wrist, to fuse at least two adjacent carpal bones 66, 68. The carpal bone surfaces may be prepared in the same fashion as described above and a trough is burred across them into which the implant is press-fit. In one form, the implant 62 can be provided in a variety of lengths and cut to measure in the operating room with a bolt cutter or rod cutter.

In one aspect, provided herein are expanded applications such as biocomposite implants, chimeric implants and xenochimeric implants. The addition of direct vascular access throughout the porous implants increases the applications of the chimeric implant technology. The porous architecture allows for vascular access at the periphery by diffusion, but prior to the addition of a more direct vascular conduit, the size of the implants that could be used was limited. An application of porous titanium foam as a scaffold for autologous chondrocyte implantation into a joint defect has been described in the prior art. This application however is limited to defects small enough to allow direct diffusion of the host blood supply through the implant. By adding a robust and dedicated vascular supply described herein, composite implants of larger size could be constructed.

Figure 5:
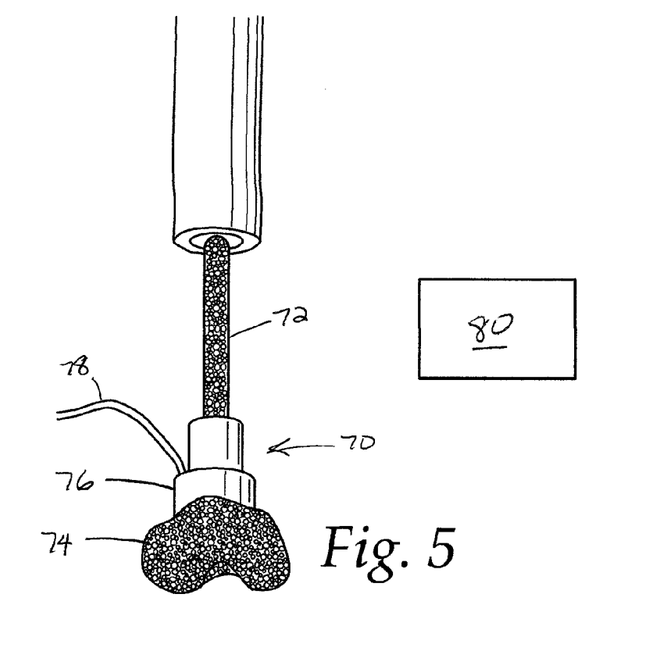
FIG. 5 is a side perspective view of one form of a portion of a replacement joint being inserted into a host bone along with an instrument fused in the process of insertion.

A further example is shown in FIG. 5. In this form, an implant device 70 is provided with a first porous implant 72 and a second porous implant 74 coupled together via a connecting structure 76. It should be noted that while the first implant 72 and the second implant 74 are shown as separate components separated by the connecting structure 76, such components may take the form of a single, integral structure, such as a single porous structure. The implant device 70 further includes a vascular conduit 78. While FIG. 5 illustrates the conduit 78 couple to the connecting structure 76, it should be noted that the conduit may also and/or alternatively coupled to the first implant 72 and/or the second implant 74. Further, multiple conduits may also be used. The device 70 may also be in the form of a kit, whereby additional sizes and shapes of conduits, tools, accessories and the like, as represented by box 80.

In one form, the implant device 70 may be suitable for a total distal femur or distal humerus replacement for unipolar arthritis or postoncologic reconstruction. A similar end-to-side anastamosis into the femoral or brachial arteries could supply the implant distally for more direct diffusion into attached autologous chondrocytes. This has an advantage over currently used techniques such as fresh-frozen osteochondral allografting as there is no immunigenic response and there is no graft resorption.

Figure 6A:
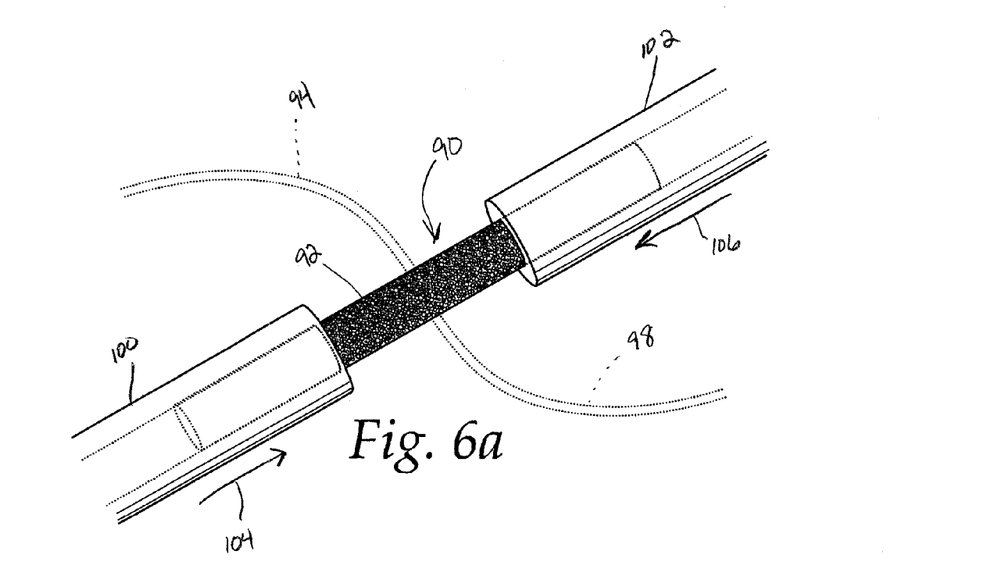
FIG. 6a is a perspective view of one form of a chimeric implant device being inserted between a host bone and a graft bone.
Figure 6B:
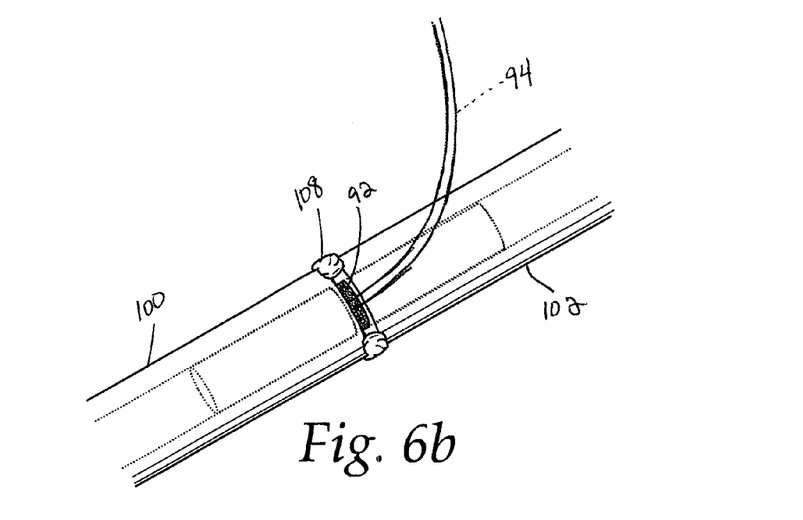
FIG. 6b is a perspective view of the chimeric implant device of FIG. 6a after the host bone and graft bone have been brought together.

Yet another example of the implant device is shown in FIGS. 6a and 6b. In this form, an implant device 90 is shown having an implant 92, such as in the form of a generally cylindrical implant, and at least one vascular conduit. As shown in FIGS. 6a and 6b, the device 90 may include a first vascular conduit 94 operably coupled to a first portion of a vascular system and/or a second vascular conduit 96 operably coupled to a second portion of a vascular system.

Such a device 90 may be used in a variety of anatomies. For example, in one form, the device 90 may be used as part of a joint or limb transplantation. According to one form, the implant 92 can be used to affix skeletal elements 100 of a transplanted limb to a host limb 102 which are then brought together, as represented by arrows 104, 106. By allowing osteocyte ingrowth of both the host and donor osteocytes into the same implant, such as shown at 108, a chimeric biocomposite implant is created, as shown in FIG. 6b. Per current research in immunomodulation for joint allotransplantation, this has the potential to induce tolerance in the host by aiding in the creation of a chimeric organ by modulating the rate of host-donor interface.

It should be understood, of course, that the foregoing relates to exemplary embodiments of the invention and that modifications may be made without departing from the spirit and scope of the invention as set forth in the following claims. By way of example, the present invention includes modifications such as drill holes or grommets for augmented fixation with screws through host bone, anti-microbial coating, and pre-seeding vascular channels with endothelial cells and growth factors. It should also be understood that ranges of values set forth inherently include those values, as well as all increments between.

What is claimed is:

1. A method of performing an orthopedic surgery to connect bone surfaces, the method comprising connecting a porous metal implant device with the vascular system of a host receiving implantation of the device, the device comprising:
   the rigid porous metal implant which is biocompatible with the mammalian body; and
   at least one implantable inlet vascular conduit comprising a biocompatible polymer, the inlet vascular conduit having first and second ends and is arranged and configured to supply blood into the implant and to connect the porous implant to a mammalian vascular system,
   the porous metal implant having internal voids which form at least 50% by volume percent of the implant, and the at least one vascular conduit providing blood flow into the porous metal implant by having the inlet vascular conduit extend into and below an outer surface of the porous metal implant to effect blood flow from a vascular system of a host receiving implantation of the device into internal portions of the porous metal implant, the blood flow effected by the vascular system of the host receiving implantation of the device after implantation, wherein the first end of the inlet vascular conduit is connected to a blood vessel and the second end of the inlet vascular conduit is below an outer surface of the rigid metal implant.

2. The method of claim 1, wherein the metal of the implant is selected from the group consisting of porous titanium, porous titanium-alloy, porous tantalum and porous tantalum-alloy implant, the metal implant having pores of 300 nm in depth and breadth and the at least one vascular conduit having a diameter in the range of from 3 mm to 9 mm.

3. The method of claim 1 wherein the metal implant has pores of 300 nm to 1300 nm depth and breadth.

4. The method of claim 1, wherein the pores have 400 nm to 800 nm depth and breadth.

5. The method of claim 1 wherein the orthopaedic procedure further comprises the step of creating a trough for placement of the implant in a press-fit fashion.

6. The method of claim 1, wherein the orthopaedic surgical procedure is selected from the group consisting of intercarpal fusion, implanting a foot prosthesis, ankle fusion, wrist fusion, knee fusion, implanting a hip and/or knee prosthesis, and limb transplants.

7. A method of performing an orthopedic surgery to connect bone surfaces, the method comprising connecting a porous metal implant device with the vascular system of a host receiving implantation of the device, the device comprising:
   the rigid porous metal implant which is biocompatible with the mammalian body;
   at least one implantable inlet vascular conduit comprising a biocompatible polymer, the inlet vascular conduit having first and second ends and is arranged and configured to supply blood into the implant and to connect the porous implant to a mammalian vascular system; and
   at least one implantable outlet vascular conduit comprising a biocompatible polymer, the outlet vascular conduit having first and second ends and is arranged and configured to couple the implant to a second portion of the vascular system and transmit blood from the implant to the second portion of the vascular system after implantation,
   the porous metal implant having internal voids which form at least 50% by volume percent of the implant, and the at least one inlet vascular conduit providing blood flow into the porous metal implant by having the inlet vascular conduit extend into and below an outer surface of the porous metal implant to effect blood flow from a vascular system of a host receiving implantation of the device into internal portions of the porous metal implant, the blood flow effected by the vascular system of the host receiving implantation of the device after implantation, wherein the first end of the inlet vascular conduit is connected to a blood vessel, the second end of the inlet vascular conduit is below an outer surface of the rigid metal implant after implantation, the first end of the outlet vascular conduit is connected to the second portion of the vascular system, and the second end of the outlet vascular conduit is coupled to the rigid metal implant.

8. The method of claim 7, wherein the metal of the implant is selected from the group consisting of porous titanium, porous titanium-alloy, porous tantalum and porous tantalum-alloy implant, the metal implant having pores of 300 nm in depth and breadth and the at least one vascular conduit having a diameter in the range of from 3 mm to 9 mm.

9. The method of claim 7 wherein the metal implant has pores of 300 nm to 1300 nm depth and breadth.

10. The method of claim 7 wherein the pores have 400 nm to 800 nm depth and breadth.

11. The method of claim 7 wherein the orthopaedic procedure further comprises the step of creating a trough for placement of the implant in a press-fit fashion.

12. The method of claim 7 wherein the orthopaedic surgical procedure is selected from the group consisting of intercarpal fusion, implanting a foot prosthesis, ankle fusion, wrist fusion, knee fusion, implanting a hip and/or knee prosthesis, and limb transplants.

\* \* \* \* \*